United States Patent [19]

Di Giorgio et al.

[11] Patent Number: Plant 7,154

[45] Date of Patent: Feb. 13, 1990

[54] CARNATION NAMED DIGIFIC

[75] Inventors: Antonio Di Giorgio; Renato Di Giorgio, both of San Remo, Italy

[73] Assignee: Laboratoire de Physiologie Vegetale, La Londe-Les Maures, France

[21] Appl. No.: 295,369

[22] Filed: Jan. 10, 1989

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new and distinct cultivar of standard carnation plant distinguished particularly by its very large blooms of a Venetian Pink color which are produced profusely during the Spring, Midseason and Fall flowering seasons on a plant having a recurrent blooming habit, the flowers being borne singly on very long, strong, upright stems from a plant reaching an average height of about 104 cm. at eight months of growth and having moderately abundant foliage.

1 Drawing Sheet

BACKGROUND OF THE NEW PLANT

This new carnation variety originated as a sport of the variety Digisun growing at our nursery at San Remo, Italy, this sport being discovered by us in 1987 and because of its delightful pink coloration contrasted with the yellow color of the blooms of the parent plant. Because of its color and its very favorable growth characteristics, we propagated this discovery at our San Remo nursery by means of cuttings with such satisfactory results that we directed continued propagation of this new plant at our nursery through several successive generations by means of successive cuttings which proved to us that the novel characteristics of this new plant would be retained from generation to generation and its homogeneity could be assured for commercial propagation for the production of cut flowers.

Our new carnation variety is now being propagated for commercial purposes by means of cuttings as well as in-vitro propagation procedures at Establissements Barberet et Blanc, Laboratoire de Physiologie Vegetale, at 83250 La Londe-Les Maures, France.

DESCRIPTION OF THE DRAWING

Our new standard carnation cultivar is illustrated by the accompanying photographic drawing which shows several blooming stems of the plant with flowers in several stages of development, together with a single stem having a bud at an early stage of opening. The color rendition being as nearly true to that herein specified as is reasonably possible to obtain by professional photographic procedures.

DESCRIPTION OF THE NEW PLANT

The following is a detailed description of our new carnation variety based upon observation of plants grown in greenhouses, as well as outside, at San Remo, Italy and also at La Londe-Les Maures, France. The color designations being according to The R.H.S. Colour Chart published by The Royal Horticultural Society of London, England.

THE PLANT

Origin: Mutation.
Parentage: The carnation variety Digisun.
Classification:

*Botanic.*—*Dianthus caryophyllus.*
*Commercial.*—Standard carnation.
Form: An erect bush having at least four stems emitted near the ground.
Height: Averages about 104 cm. at eight months of growth.
Main stem: Length: Less than 15 cm. due to pinching.
Branching character: The plant is well-branched.
Growth: Vigorous, upright and rigid.
Foliage:
- Quantity.—Moderately abundant.
- Number of leaves.—More than 120.
- Leaf size.—(At the seventh node) Averages about 12.5 cm. long and about 1 cm. wide.
- Leaf shape.—Linear with acuminate apex and entire margins.
- *Texture.*—Leathery.
- *Color.*—Both upper and under sides, between 189-A and 147-A.
- *Ribs and veins.*—Hardly noticeable.
- *Rachis.*—Hardly noticeable.
- *Leaflets.*—None.

THE BUD

Size: Large.
- *Diameter.*—Averages about 2.6 cm.
- *Length.*—Averages about 2.6 cm.

Shape: Generally ovoid.
Rate of opening: Normal.
Color of petals: When sepals first divide and when the petals begin to unfurl — Venetian Pink, 49-B.
Sepals:
- *Number.*—Five.
- *Shape.*—Generally ovoid with acuminate apex and joined together at the lower parts.
- *Character.*—The sepals are hooded over the bud and curl back when the flower opens.
- *Color.*—Inside, 145-C. Outside, 145-B and 143-C.
- *Striae.*—Longitudinal.

Calyx:
- *Size.*—Large.
- *Shape.*—Funnel-shaped.
- *Splitting.*—Very little.
- *Aspect.*—Smooth.

Flower stem:
- *Length.*—Averages about 90 cm.

*Character.*—Rigid and erect.
*Color.*—Between 189-A and 147-A.

THE FLOWER

Blooming habit: Recurrent and blooming profusely during the Spring, Midseason and Fall blooming periods, with a tendency to give few blooms in the fall.
Size of flower: Very large.
*Diameter.*—Averages about 8.5 cm.
*Depth.*—Averages about 5.5 cm.
Borne: Singly on a long, strong, upright stem.
Shape: When bloom first opens, high-centered. When bloom matures, dome-shaped.
Petalage:
*Number of petals.*—Averages 102.
*Arrangement.*—Imbricated.
*Form.*—Fan-shaped with rounded and very serrated margins.
*Texture.*—Leathery.
*Aspect.*—Satiny.
*Color.*—Both inside and outside petals: Body — 49-A/B. Base — Greenish White. Reverse Side — 49-A/B.
*Petaloids.*—Number: Less than eight. Size: Smaller than the petals. Color: The same as the petals.
Flower stem: Averages 90 cm. (cut at tenth node).
*Character.*—Upright with good strength.
*Color.*—Between 147-A and 189-A.
Discoloration after full bloom: Very little.

Persistence: The flower petals hang on and dry.
Fragrance: Perceptible.
Lasting quality: As a cut flower, at least ten days in vase keeping.

REPRODUCTIVE ORGANS

Stamens:
*Number.*—Six to twelve.
*Arrangement.*—Around the ovary.
*Anthers.*—Size: Less than 4 mm. Color: Whitish.
*Filaments.*—Length: Averages about 3 cm. Color: White.
Pistils:
*Number.*—Two.
*Styles.*—Length: About 2.5 cm. Color: Whitish.
*Stigma.*—Color: Slightly pink.
Character of ovaries: Ribbed.

In general, this new variety most nearly resembles its parent, Digisun, but differs, however, by having a plain, bright pink flower color.

We claim:

1. The new and distinct standard carnation cultivar, substantially as herein shown and described, particularly characterized by its very large flowers having a Venetian Pink color, the plant having a profuse production of flowers grown on strong, upright stems with moderately abundant foliage during its recurrent flowering periods.

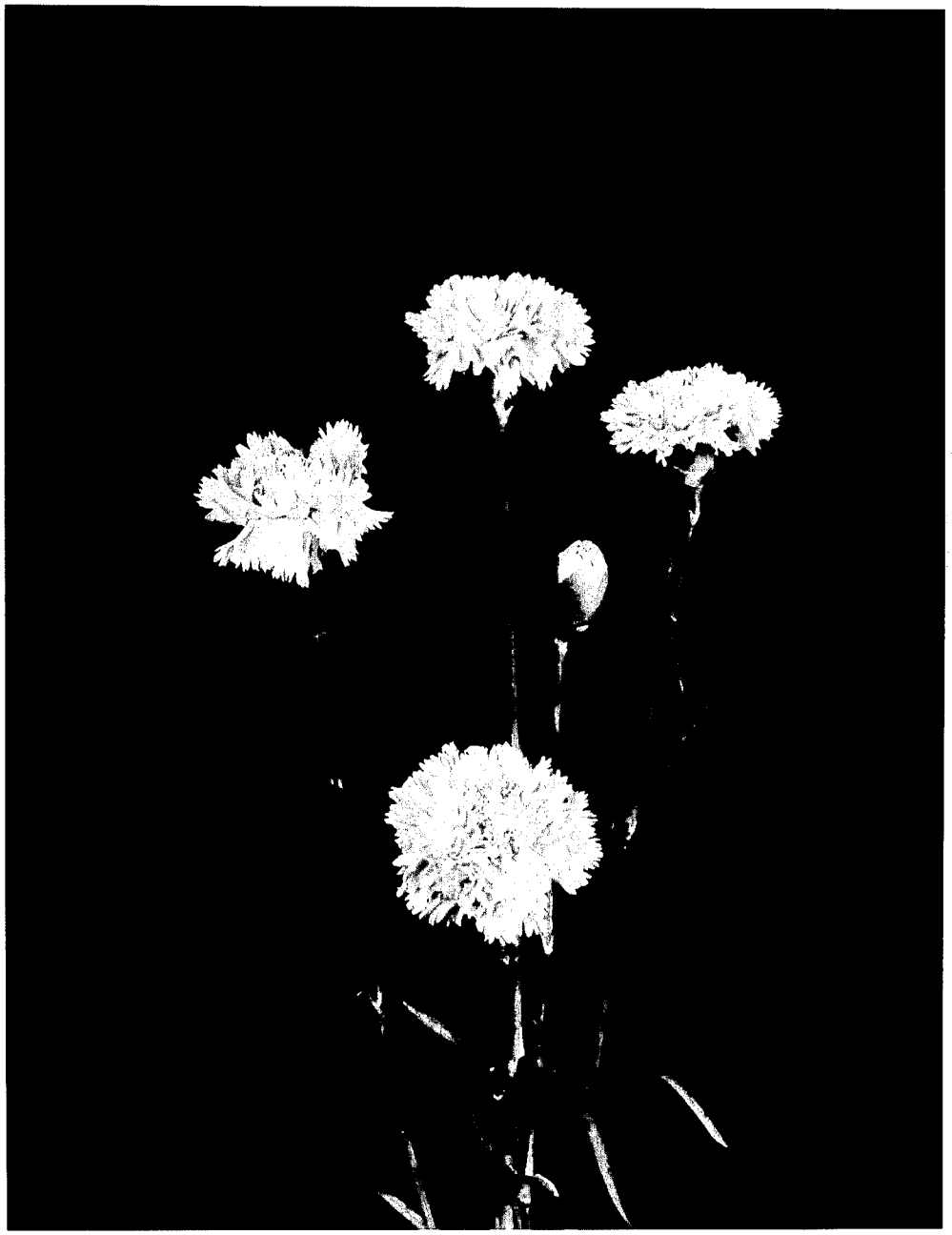

* * * * *